(12) United States Patent
Penttila et al.

(10) Patent No.: US 9,066,526 B2
(45) Date of Patent: Jun. 30, 2015

(54) ALLERGY TREATMENT USING ACID TREATED AQUEOUS WHEY PROTEIN EXTRACT

(75) Inventors: Irmeli Auli Penttila, Athelstone (AU); Ian Robert Mitchell, Berwick (AU)

(73) Assignee: Dairy Australia Limited, Southbank (AU)

( * ) Notice: Subject to any disclaimer, the term of this patent is extended or adjusted under 35 U.S.C. 154(b) by 0 days.

(21) Appl. No.: 13/501,819

(22) PCT Filed: Oct. 14, 2010

(86) PCT No.: PCT/AU2010/001355
§ 371 (c)(1),
(2), (4) Date: Apr. 13, 2012

(87) PCT Pub. No.: WO2011/044628
PCT Pub. Date: Apr. 21, 2011

(65) Prior Publication Data
US 2012/0201839 A1    Aug. 9, 2012

(30) Foreign Application Priority Data
Oct. 16, 2009 (AU) ................................ 2009905062

(51) Int. Cl.
| A61K 38/00 | (2006.01) |
|---|---|
| A61K 39/00 | (2006.01) |
| A61K 39/38 | (2006.01) |
| A23J 1/02 | (2006.01) |
| A23J 1/04 | (2006.01) |
| C07K 1/00 | (2006.01) |
| C07K 14/00 | (2006.01) |
| C07K 16/00 | (2006.01) |
| C07K 17/00 | (2006.01) |
| C08H 1/00 | (2006.01) |
| A23C 21/00 | (2006.01) |
| A23L 1/29 | (2006.01) |
| A23L 1/305 | (2006.01) |
| A61K 35/20 | (2006.01) |
| A61K 38/01 | (2006.01) |

(52) U.S. Cl.
CPC ............... *A23C 21/00* (2013.01); *A23L 1/296* (2013.01); *A23L 1/3056* (2013.01); *A23V 2002/00* (2013.01); *A61K 35/20* (2013.01); *A61K 38/018* (2013.01)

(58) Field of Classification Search
None
See application file for complete search history.

(56) References Cited

U.S. PATENT DOCUMENTS

| 3,922,375 A * | 11/1975 | Dalan et al. | 426/583 |
|---|---|---|---|
| 4,071,406 A * | 1/1978 | Kanda | 435/104 |
| 2002/0044998 A1* | 4/2002 | Wu | 426/583 |

FOREIGN PATENT DOCUMENTS

| AU | 2002329364 B8 | 1/2003 |
|---|---|---|
| DE | 19918210 A1 | 11/2000 |
| DE | 19950240 | 5/2001 |
| EP | 0311283 | 4/1989 |
| EP | 1514482 B1 | 9/2008 |
| WO | WO 96/32021 A1 | 10/1996 |
| WO | WO 2009/026188 A1 | 2/2009 |

OTHER PUBLICATIONS

Velaphi S.C., et al, "Growth and Metabolism of Infants Born to Women Infected with Human Immunodeficiency Virus and Fed Acidified Whey-Adapted Starter Formulas", Nutrition, 2008, vol. 24, No. 3, pp. 203-211.
Penttila, I., "Effects of Transforming Growth Factor-Beta and Formula Feeding on Systemic Immune Responses to Dietary Beta-Lactoglobulin in Allergy-Prone Rates", Pediatric Research, 2006, vol. 59, No. 5, pp. 650-655.
Von Berg, A., "Modified Proteins in Allergy Prevention", Nestle Nutrition Institute Workshop Series Pediatric Program, 2009, vol. 64, pp. 239-247, discussion 247-257, e-publication, Aug. 19, 2009, See in particular—Abstract, p. 239, lines 6-8, p. 240, lines 7-10, p. 240, lines 14-19, p. 240, lines 23-24, p. 240 , lines 28-29, p. 240, line 35-36, p. 245, lines 32-34.
Penttila, Irmeli A. et al: "Immune modulation in suckling rat pups by a growth factor extract derived from milk whey", Journal of Dairy Research, Cambridge University Press, Cambridge, GB, vol. 68, No. 4, Nov. 2001, pp. 587-599, XP009096149, ISSN: 0022-0299, DOI: 10, 1017/S0022029901005180.
Rogers, M-L et al: "Transforming growth factor beta in bovine milk: Concentration, stability and molecular mass forms", Journal of Endocrinology, Society for Endocrinology, GB, vol. 151, No. 1, Oct. 1996, pp. 77-86, XP0000644717, ISSN: 0022-0795, DOI: 10,1677/JOE.0.1510077.
European Extended Search Report and Opinion dated Dec. 17, 2013.

* cited by examiner

*Primary Examiner* — Nora Rooney
(74) *Attorney, Agent, or Firm* — Faegre Baker Daniels LLP (57) ABSTRACT

The invention relates to manufacture of whey protein extracts, to infant formula and to reducing or preventing food allergy. The whey protein extract is produced from a whey protein-containing composition by contacting a whey protein-containing composition with an aqueous solution to form a sample including a soluble protein-containing component and an insoluble component; recovering the soluble protein-containing component from the sample; and acidifying the soluble protein-containing component, thereby producing the whey protein extract. Extracts produced by the method of the invention may be used in infant formula, as a dietary supplement or foodstuff.

8 Claims, 6 Drawing Sheets

ND STATES PATENT

ALLERGY TREATMENT USING ACID TREATED AQUEOUS WHEY PROTEIN EXTRACT

CROSS-REFERENCE TO RELATED APPLICATIONS

This application is a nationalization of PCT Patent Application Serial No. PCT/AU2010/001355, filed Oct. 16, 2010, which claims the benefit of Australian Patent Application No. 2009905062 filed Oct. 16, 2009, the disclosures of which are expressly incorporated herein by reference.

FIELD OF THE INVENTION

The invention relates to manufacture of whey protein extracts, to infant formula and to reducing or preventing food allergy.

BACKGROUND OF THE INVENTION

Infants who are not fed at the breast must rely on infant formula as their source of nutrients and to help ensure normal growth and developments.

Infant formula is commonly based on the milk of cows. However about 2 to 3% of infants have an allergy to the protein in cow's milk. While there are a number of factors that regulate immune responses to allergens, the Th1/Th2 balance in infants is important in immune development, and formula is deficient in cytokines which promote immune regulatory mechanisms and drive Th1 and Th2 differentiation. As such, there is a need for a dietary supplement, foodstuff or infant formula that promotes appropriate immune responses and development.

SUMMARY OF THE INVENTION

In one embodiment there is provided a process for the production of a whey protein extract from a whey protein-containing composition including:
contacting a whey protein-containing composition with an aqueous solution, thereby forming a sample including a soluble protein-containing component and an insoluble component;
recovering the soluble protein-containing component from the sample;
acidifying the soluble protein-containing component;
thereby forming the whey protein extract.

In another embodiment there is provided a process for the production of a whey protein extract from a whey protein-containing solution including:
separating soluble whey protein from insoluble whey protein in a whey protein-containing solution;
acidifying the soluble whey protein;
thereby forming the whey protein extract.

In another embodiment there is provided a whey protein extract including an acid treated aqueous soluble whey protein-containing component. In certain embodiments, the extract is produced according to the above described process.

In other embodiments there is provided a use of a whey protein extract including an acid treated aqueous soluble whey protein-containing component for the manufacture of an infant formula, dietary supplement or foodstuff.

In related embodiments there is provided an infant formula, dietary supplement or foodstuff including a whey protein extract including an acid treated aqueous soluble whey protein-containing component.

In further embodiments there is provided a use of a whey protein extract including an acid treated aqueous soluble whey protein-containing component for the manufacture of a medicament for preventing or minimising food allergy.

In another embodiment there is provided a method for preventing or minimising food allergy including the step of providing a whey protein extract including an acid treated aqueous soluble whey protein-containing component to an individual.

In further embodiments there is provided a method for reducing the release of TNF or IL-2 in an individual predisposed to food allergy including the step of providing a whey protein extract including an acid treated aqueous soluble whey protein-containing component to the individual. In yet further embodiments there is provided a method for increasing the release of IL-18 in an individual predisposed to food allergy including the step of providing a whey protein extract including an acid treated aqueous soluble whey protein-containing component to the individual.

In still further embodiments there is provided a method for enhancing the intestinal epithelial cell barrier function in an individual predisposed to food allergy including the step of providing a whey protein extract including an acid treated aqueous soluble whey protein-containing component to the individual.

In still further embodiments there is provided a method for enhancing a Th1 immune response in an individual predisposed to food allergy including the step of providing a whey protein extract including an acid treated aqueous soluble whey protein-containing component to the individual.

In another embodiment there is provided a method for minimising a Th2 immune response in an individual predisposed to food allergy including the step of providing a whey protein extract including an acid treated aqueous soluble whey protein-containing component to the individual.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

The inventor has surprisingly found that a whey protein extract in the form of an acid treated aqueous soluble whey protein-containing component has immuno regulatory properties. In particular, the in vitro studies described herein show that the extract (otherwise known as 'I23') increases biomarkers that are characteristic of a Th1 response while minimising markers of a Th2 response. Specifically, these in vitro studies show that the extract decreases IL-2 secretion by $CD4^+$ T cells and increases IL-18 and TNF secretion. Importantly the studies show that the extract enhances intestinal barrier function.

Further, to the above, the in vivo studies herein show that the extract minimises total serum IgE, anti BLG IgG1 and mast cell count in formula fed allergy prone individuals. Still further, the in vivo studies herein show that the extract minimises total serum IgE during weaning of allergy prone individuals. These findings demonstrate the utility of the extract in immune regulation in allergy prone individuals during formula feeding and weaning.

A whey protein extract comprising an acid treated aqueous soluble whey protein-containing component may be produced by a process involving solubilisation of whey protein-containing composition and acidification of the aqueous soluble component of the composition.

Thus in certain embodiments there is provided a process for the production of a whey protein extract from a whey protein-containing composition. The process includes the following steps:

contacting a whey protein-containing composition with an aqueous solution, thereby forming a sample including a soluble protein-containing component and an insoluble component;

recovering the soluble protein-containing component from the sample;

acidifying the soluble protein-containing component; thereby forming the whey protein extract.

In other embodiments the whey protein extract may be produced by a process in which an aqueous soluble whey (such as a liquid whey) is acidified. Thus in another embodiment there is provided a process for the production of a whey protein extract from a whey protein-containing solution including:

separating soluble whey protein from insoluble whey protein in a whey protein-containing solution;

acidifying the soluble whey protein;

thereby forming the whey protein extract.

The above described methods may include an additional step of neutralizing the acidified soluble whey protein.

'Whey' is generally the serum or watery fraction of milk that forms along with curd formation when milk coagulates. Whey is typically formed in cheese production when curd forms. Whey is rich in lactose, minerals, and vitamins and contains lactalbumin and traces of fat.

Whey may be formed from any mammalian milk, preferably cow, goat or sheep milk, more preferably cow milk.

'Whey protein' is generally the protein that is found in whey. It may be provided in the form of a solid, liquid or concentrate.

A 'whey protein-containing composition' is generally a composition that includes whey proteins. In some embodiments, the whey protein-containing composition consists of whey protein. In these embodiments, the composition substantially lacks proteins that are not found in whey, although the composition may include other non protein components such as carbohydrate and fat. Examples include whey protein concentrates (WPC) and whey protein isolates (WPI). WPC and WPI and processes for producing these compositions are described further herein.

In other embodiments, the whey protein-containing composition includes proteins not generally found in whey. Examples include casein protein. These other proteins may be added together with whey protein to form the whey-protein containing composition. Alternatively these proteins may be comprised in the whey protein-containing composition as the composition is formed. Examples of the latter formed composition include milk and milk products.

In one embodiment, the whey protein-containing composition may be enriched for whey protein. For example, whey protein may be added to a whey protein-containing composition to increase the relative abundance of whey protein in the composition. In other embodiments, non whey protein, or other non protein components may be removed from a whey protein-containing composition, thereby increasing the relative abundance of whey protein in the composition. Examples of processes for enriching for whey protein including filtration are described further herein.

In one embodiment, the whey protein-containing composition may be enriched for a particular protein species. Particular protein species of interest are those that have application in immune regulation and in particular, proteins that are useful for minimising or preventing allergy. Examples include proteins that tend to mediate a Th1 immune response in preference to a Th2 response. One example is TGF beta.

In one embodiment the whey protein-containing composition may include a peptide useful for inducing tolerance to dietary protein that is newly introduced to a mammal at weaning.

In one embodiment the protein component of the whey protein-containing composition may be partially or extensively hydrolysed. A 'partially hydrolysed whey protein-containing composition' generally contains oligopeptides that have a molecular weight of generally less than 5000 d. An 'extensively hydrolysed whey protein-containing composition' generally contains peptides that have a molecular weight of less than 3000 d.

In one embodiment, the whey protein-containing composition may contain a physiologically acceptable salt, pH buffering agent, preservative or anti-microbial agent.

In one embodiment, the whey protein-containing composition includes one or more of sweet whey, acid whey, reduced lactose whey, demineralised whey, WPC or WPI.

'Sweet whey' may be derived from the manufacture of cheeses such as Cheddar, Mozzarella and Swiss that has been pasteurized and to which no preservatives have been added. Sweet whey powder generally contains all the constituents of fresh whey, except water in the same relative proportion. Typically, sweet whey powder has about 11-14.5% protein, about 63 to 75% lactose, about 1 to 1.5% fat, about 8.2 to 8.8% ash and about 3.5 to 5% moisture.

'Acid whey' may be derived from the manufacture of cheeses such as cottage, cream cheese and ricotta that has been pasteurized and to which no preservatives have been added. Acid whey powder contains all the constituents of original acid whey, except water, in the same relative proportion. Typically, acid whey powder has about 11-13.5% protein, about 61 to 70% lactose, about 0.5 to 1.5% fat, about 9.8 to 12.3% ash and about 3.5 to 5% moisture. Acid whey may be neutralised before use in the invention described herein.

'Reduced lactose whey' may be obtained by the selective removal or hydrolysis of lactose from whey. The lactose content of the dry product may not exceed 60%. Reduction of lactose may be accomplished by physical separation techniques such as precipitation or filtration or enzymatic hydrolysis of lactose to glucose and galactose. The acidity of reduced lactose whey may be adjusted by the addition of safe and suitable ingredients. Typically, reduced lactose whey powder has about 18-24.0% protein, about 52 to 58% lactose, about 1 to 4% fat, about 11 to 22% ash and about 3 to 4% moisture.

Demineralised whey (also called 'reduced-minerals' whey) is obtained by removing a portion of the minerals from pasteurized whey. Typical levels of demineralization are 25%, 50% and 90%. The dry product may not exceed 7% ash. Demineralised whey may be produced by separation techniques such as ion exchange, diafiltration or electrodialysis. The acidity of demineralised whey may be adjusted by the addition of safe and suitable ingredients.

WPCs, are concentrates of whey having specified amounts of protein. Generally, WPC34 specifies a concentrate having not less than 34% protein, WPC50 specifies a concentrate having not less than 50% protein, WPC60 specifies a concentrate having not less than 60% protein, WPC75 specifies a concentrate having not less than 75% protein and WPC80 specifies a concentrate having not less than 80% protein. These concentrates may be formed by ultrafiltration of pasteurised whey, recovery of the retentate, followed by concentration and spray drying of the retentate to form WPC34 and WPC50 powder; or diafiltration of the retentate, followed by concentration and spray drying to form WPC50, WPC60, WPC75 or WPC80.

WPI is obtained by removing sufficient non protein constituents from whey so that the finished dry product contains not less than 90% protein. WPI is produced by membrane separation processes or ion exchange. In one example, pasteurized fluid whey is subjected to microfiltration resulting in removal of lipids, diafiltration is then applied to form a permeate and whey protein isolate and the latter is then concentrated and spray dried to form WPI powder. In another example, pasteurized fluid whey is subjected to ion exchange protein separation leading to deproteinated whey and the adsorbed whey protein is then desorbed, subjected to ultrafiltration or further ion exchange to remove minerals. The whey protein isolate so formed is then subjected to concentration and spray drying to form WPI powder.

In one embodiment, the amount of protein in the whey protein-containing composition is at least about 10% w/w on a dry weight basis.

In one embodiment, the amount of protein is about 10% to less than about 90% w/w.

In one embodiment, the amount of protein is about 11% to about 25% w/w.

In one embodiment, the amount of protein is about 11% to about 18% w/w.

In one embodiment, the amount of protein is about 18% to about 25% w/w.

In one embodiment, the amount of protein is about 34% to about 80% w/w.

In one embodiment, the amount of protein is about 50% to about 75% w/w.

In one embodiment, the amount of protein is about 50% to about 60% w/w.

In one embodiment, the amount of protein is about 60% to about 75% w/w.

In one embodiment, the amount of protein is about 90% to about 95% w/w.

In one embodiment, the whey protein-containing composition includes at least one of carbohydrate (such as lactose) and fat.

In one embodiment, the amount of lactose in the whey protein-containing composition is at least about 1% w/w on a dry weight basis.

In one embodiment, the amount of lactose is about 1% to less than about 80%.

In one embodiment, the amount of lactose is about 63% to about 75% w/w.

In one embodiment, the amount of lactose is about 61% to about 70% w/w.

In one embodiment, the amount of lactose is about 52% to about 58% w/w.

In one embodiment, the amount of lactose is about 70% to about 80% w/w.

In one embodiment, the amount of lactose is about 48% to about 52% w/w.

In one embodiment, the amount of lactose is about 33% to about 37% w/w.

In one embodiment, the amount of lactose is about 25% to about 30% w/w.

In one embodiment, the amount of lactose is about 10% to about 15% w/w.

In one embodiment, the amount of lactose is about 4% to about 8% w/w.

In one embodiment, the amount of lactose is about 0.5% to about 1.0% w/w.

In one embodiment, amount of fat in the whey protein-containing composition is at least about 0.5% w/w on a dry weight basis.

In one embodiment, the amount of fat is about 0.5% to less than about 10% w/w.

In one embodiment, the amount of fat is about 1% to about 5% w/w.

In one embodiment, the amount of fat is about 5% to about 7% w/w.

In one embodiment, the whey protein-containing composition includes about 80 to 82% protein, about 4 to 8% lactose and about 4 to 8% fat w/w.

In one embodiment, the whey protein-containing composition is a WPC.

In one embodiment, the WPC is WPC80. Other WPCs include WPC34, WPC50, WPC60 and WPC75.

In one embodiment, the whey protein-containing composition is provided in the form of a powder for contact with the aqueous solution.

An 'aqueous solution' also known as 'aqueous solvent' is a water-based component that can be used for completely or partially dissolving whey protein. The aqueous solution may be water, including purified, distilled or sterilised water. The aqueous solution may contain physiologically acceptable salts. Examples of these salt containing solutions include saline. The aqueous solution may contain a pH buffering agent or preservative or anti-microbial agent.

An 'aqueous soluble protein-containing component' or 'fraction' is generally a component or fraction of the sample that contains proteins dissolved completely or partially in the aqueous solvent. This may also be referred to as an 'aqueous solubilised protein-containing component' or 'aqueous solubilised protein-containing fraction'. Proteins that dissolve completely in an aqueous solvent tend to be ones that adopt a conformation in solution whereby hydrophobic or non polar side chains and groups are buried within the protein out of contact with the solution and polar or hydrophilic side chains are exposed at the protein surface for contact with the solvent. Proteins that dissolve partially in an aqueous solvent may adopt a conformation in solution whereby some of the hydrophobic side chains or groups are exposed on the protein surface to the solvent.

In one embodiment, the whey protein-containing composition is contacted with the aqueous solution in conditions for enhancing the formation of the solubilised protein-containing component. For example, the mixture of the solution and the composition may be agitated or stirred using known methods. Temperature may be adjusted to enhance complete or partial solubilisation. One or more agents for assisting with solubilisation may be added to the mixture.

In one embodiment, the whey protein-containing composition is provided for contact with the aqueous solution in an amount of at least about 0.5% whey protein-containing composition w/w.

In one embodiment, the whey protein-containing composition is provided in an amount of about 0.5% to 10% w/w.

In one embodiment, the whey protein-containing composition is provided in an amount of about 0.5% to 7% w/w.

In one embodiment, the whey protein-containing composition is provided in an amount of about 5% to 6% w/w.

Typically the completely or partially solubilised proteins in the component are whey proteins, although there may also be other milk derived proteins in the component, depending on the whey protein-containing composition forming the starting or feed material for the process.

An 'insoluble component' component formed in the process generally contains protein, fat or ash. Generally, the insoluble component is not dissolved when the aqueous solution is agitated, stirred or temperature adjusted.

Generally, a larger amount of insoluble component forms where the whey protein-containing composition is provided in larger amounts of composition per amount of solution.

Generally the insoluble component has a paste like texture and a white or whitish colour.

Generally the insoluble component settles to the bottom of a vessel in which the whey protein-containing component is contacted with the aqueous solvent. The settling may occur with or without centrifugation.

The solubilised protein-containing component may be recovered by separating the solubilised protein-containing component from the insoluble solid. Generally, substantially all of the solubilised protein-containing component is recovered. In some embodiments, substantially all of the solubilised protein-containing component is separated from the insoluble solid. While not wanting to be bound by hypothesis, it is believed that the separation of the insoluble component from the aqueous soluble component is important as the former might contain molecules that suppress a Th1 immune response or that disrupt barrier function.

The separation process may be a single step of multi-step process.

Any number of techniques known in dairy processing for separating a complete or partially soluble fraction such as a supernatant from a solid may be used to separate the solubilised protein-containing component from the insoluble solid. Examples include decanting, centrifugation, chromatography (ion exchange, gel filtration, HPLC, RP-HPLC, affinity), electrodialysis, filtration or adsorption.

Typically the solubilised protein-containing component is acidified by providing a pH of at least about 2.5, preferably about 3 to 6.0, more preferably about 3.0 to 5.5, 3.5 to 5.0, to the solubilised protein-containing component.

While not wanting to be bound by hypothesis, it is believed that the acidification step activates TGF beta in the aqueous soluble component by removing the LAP peptide.

It will be understood that the acidification step may be carried out before recovery of the solubilised protein-containing component from the sample, although typically it is carried out after recovery, in which case an acid is provided to the solubilised protein-containing component.

Accordingly, there is provided a process for the production of a whey protein extract from a whey protein-containing composition including the following steps in order:

contacting a whey protein-containing composition with an aqueous solution, thereby forming a sample including a soluble protein-containing component and an insoluble component;

recovering the soluble protein-containing component from the sample;

acidifying the soluble protein-containing component thereby producing the whey protein extract.

Typically the solubilised protein-containing component is neutralised by providing a pH of about 6.5 to 7.5 preferably about 7 to the solubilised protein-containing component.

The neutralisation step may be carried out before recovery of the solubilised protein-containing component from the sample although generally it is carried out after the solubilised protein-containing component has been recovered from the sample and acidified.

The whey protein extract described above may be provided in liquid or solid form. Typically it is provided in solid form, such as a powder. Thus in certain embodiments, the above described process includes the further step of drying the solubilised protein-containing component, thereby obtaining a powder. Suitable drying methods are well known to the skilled worker. Evaporation, including vacuum concentration, spray drying, roller and drum drying are examples.

The whey protein extract comprising an acid treated aqueous soluble whey protein-containing component, including one formed by a method as described above, may be further processed or modified before use. Any one of the following processes or modifications may be applied:
- enrichment, concentration or fractionation of whey protein, for example using membrane filtration technology discussed further herein;
- enzymatic hydrolysis to partially or extensively hydrolyse protein contained in the extract;
- mineral or ash removal, for example using electrodialysis technology further discussed herein;
- removal of non protein components using chromatography or crystallisation technologies further described herein;
- addition of immunoregulatory molecules such as TGF beta;
- addition of peptide antigen useful for inducing tolerance to newly received dietary protein during weaning;
- further drying
- sizing of granules.

Membrane technologies including reverse osmosis, nanofiltration, ultrafiltration and microfiltration may involve a pressure-driven separation using a semi-permeable membrane whereby a combination of pumps and valves creates a pressure gradient across the membrane which drives the smaller molecules in the whey across the membrane, thereby concentrating the larger molecules and particles that cannot cross the membrane. Selective separation or concentration can be achieved by using membranes with different pore sizes or molecular weigh cut-off. Examples of membranes include those used in reverse osmosis (RO), nanofiltration (NF), ultrafiltration (UF) and microfiltration (MF). FR membranes have the smallest pores and allow only water to cross the membrane while all other components of the whey are retained. A common use of RO membranes is water desalination. These membranes are generally rated according to their ability to reject salt. Like vacuum concentration, RO systems do not change the ratios of the solid components of the whey but rather concentrate the solid components by removing only water. The extent of whey concentration by RO is limited by the increase in viscosity and osmotic pressure of the whey as water is removed.

Nanofiltration membranes are sometimes referred to as "loose" RO membranes. NF membranes allow some monovalent ions to cross the membrane along with the water resulting in a partial "desalting" of the whey. Because only minerals with a single charge are removed, NF membranes only slightly reduce the mineral content of whey. NF membranes may be used to reduce the sodium chloride content of some types of whey.

Ultrafiltration membranes have larger pores than RO or NF membranes. UF membranes permeate lactose and ash while retaining the proteins in whey thereby making UF membranes the standard tool for production of WPCs. The greater the amount of lactose and ash removed, the higher the protein content of the WPC. Because the viscosity of the whey increases as protein concentrate increases, addition of water to the retentate to wash out additional amounts of lactose and minerals, in a process known as diafiltration, is necessary when producing WPCs with more than 50% protein.

Microfiltration membranes have the largest pores of the membrane separation processes. Smaller soluble proteins, peptides, lactose, minerals, non-protein nitrogen components, and water readily permeate MF membranes. Fat globules are retained by MF membranes therefore these membranes can be used to remove the small amounts of fat that are not recovered by centrifugation. Trace amounts of fat must be removed to produce WPIs.

Electrodialysis also uses semi-permeable membranes, however, an electrical current replaces pressure as the driving force for separating whey components. Electrodialysis membranes allow only minerals to permeate while retaining lactose and proteins. An electrical current draws the charged mineral ions through the membranes and into a brine stream. Lactose is not affected by the current and proteins cannot cross the membranes. Electrodialysis does not denature whey proteins while removing up to 75% of the minerals in whey.

Ion exchange is a type of chromatography. For example, when producing demineralized whey, whey passes through a column containing absorbent beads that bind the ions (charged minerals) in the whey. The remainder of the whey components such as protein and lactose pass through the column unhindered. The resulting whey therefore will have reduced amounts of minerals as compared to untreated whey. Ion exchange does not denature proteins and can remove up to 98% of the minerals in whey.

Chromatography processes use charged resins to separate proteins in whey from other components. The proteins bind to oppositely charged resin while components like lactose do not bind and therefore pass directly through the system. After the whey has passed through the column or tank containing the resin, a buffer is sent through the system to release the bound proteins. The proteins can be purified further by UF and then spray dried.

Chromatography can also be used to separate specific proteins from other proteins in whey. Lactoferrin and lactoperoxidase are positively charged at a pH typical for sweet whey. The major proteins of whey, Alpha-lactalbumin, Beta-lactoglobulin and bovine serum albumin are negatively charged at the same pH. When whey passes through a tank containing negatively charged resin, the positively charged lactoferrin and lactoperoxidase bind to the resin while the other proteins and whey constituents pass through the column. An alkaline solution is then sent through the column to release the bound proteins from the resin. The recovered proteins can then be washed and spray dried.

Crystallization is used to produce either lactose or non-hygroscopic whey/permeate powder. Whey or permeate is concentrated to at least 50% total solids by evaporation where lactose is supersaturated such that the lactose will readily crystallize as the concentrated whey/permeate is cooled. After the whey/permeate has cooled sufficiently, the lactose crystals can be removed for further processing into high quality lactose, or the whey/permeate solution with crystallized lactose can be dried to produce non-hygroscopic whey/permeate powder.

Beta-galactosidase, an enzyme, can be added to whey to hydrolyze the disaccharide lactose into its component monosaccharides, glucose and galactose. Time and temperature are used to control the degree of lactose hydrolysis.

Proteases are enzymes added to whey to hydrolyze the proteins. The type of protease added, time and temperature are used to control the type and degree of protein hydrolysis.

In principle, protein modification by hydrolysis is the opposite of polymerization. Proteases are the most common group of enzymes used to cleave the peptide bonds of a protein molecule, resulting in smaller peptides and polypeptides. The degree of hydrolysis, i.e., the degree to which the whey proteins are hydrolyzed, will affect the functional properties of the hydrolysates as food ingredients.

Whey proteins can be denatured by heat to alter their functional properties. A combination of time and temperature is used to control the amount of whey protein denaturation. Controlled denaturation often is done during the preheating treatment. The amount of undenatured whey protein can be measured by the whey protein nitrogen index.

In one embodiment there is provided a use of an extract described above for the manufacture of an infant formula, follow on formula, dietary supplement or foodstuff.

An infant formula is generally a nutritional composition given to newly born individuals in place of breast milk. An infant formula may be given to about 4 to 6 months of age.

A follow on formula is generally a nutritional composition given to individuals from about 6 months of age or older.

The formula may be prepared in any suitable manner. For example, it may be prepared by blending together the whey protein extract described herein, together with other nutritional components such as a carbohydrate source, or fat source in appropriate proportions. If used, the emulsifiers may be included at this point. Other components such as immune regulatory molecules, vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

If a liquid product is preferred, the homogenised mixture may be sterilised then aseptically filled into suitable containers. In other embodiments the product may be treated in a way to extend shelf life such as through heat treatment.

In one embodiment there is provided an infant formula, dietary supplement or foodstuff including an extract described above.

A formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate source contributes between 35 and 65% of the total energy of the formula.

A follow-on formula according to the present invention may contain a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The follow-on formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the formula may contain emulsifiers and stabilisers such as soy lecithin, citric acid esters of mono- and di-glycerides, and the like.

The formula may optionally contain other substances which may have a beneficial effect such as lactoferrin, nucleotides, nucleosides, and the like.

Finally, the formula may contain indigestible oligosaccharides such as galacto-oligosaccharides for example in an amount of from 0.3 to 7%.

Examples of formula are discussed in Koletzko B et al. 2005 *J. Pediatric Gastroenterol Med.* 41:584-599.

In certain embodiments, the extract is provided to an individual in an amount of 2.3 g/kg body weight of the individual.

In one embodiment there is provided a use of an acid whey for the manufacture of an infant formula, follow on formula, dietary supplement or foodstuff, and a formula, supplement or food stuff containing an acid whey. In these embodiments, the acid whey effectively substitutes for the whey protein extract including an acid treated aqueous soluble whey protein containing-component described herein. In these embodiments, the acid whey may be neutralized before use.

In one embodiment there is provided a use of an extract described herein for the manufacture of a medicament for preventing or minimising food allergy.

In one embodiment there is provided a method for preventing or minimising food allergy including the step of providing an extract described herein to an individual. Typically the individual is a human. Typically the human is pre-disposed to allergy. Typically the human is a neonate. Typically the neonate is less than about 2 years old.

In one embodiment there is provided a method for reducing the release of TNF or IL-2 in an individual predisposed to food allergy including the step of providing an extract of claim 48 to the individual.

In one embodiment there is provided a method for increasing the release of IL-18 in an individual predisposed to food allergy including the step of providing an extract of claim 48 to the individual.

In one embodiment there is provided a method for enhancing the intestinal epithelial cell barrier function in an individual predisposed to food allergy including the step of providing an extract described herein to the individual.

In one embodiment there is provided a method for enhancing a Th1 immune response in an individual predisposed to food allergy including the step of providing an extract described herein to the individual.

In one embodiment there is provided a method for minimising a Th2 immune response in an individual predisposed to food allergy including the step of providing extract described herein to the individual.

In the above described methods, acid whey may effectively substitute for the whey protein extract including an acid treated aqueous soluble whey protein containing-component described herein.

The examples that follow are intended to illustrate but in no way limit the present invention.

EXAMPLES

Example 1

Production of a Whey Protein Extract Including an Acid Treated Aqueous Soluble Whey Protein-Containing Component 200 ml $H_2O$ as added to 12 g of WPC 80 and incubated for 30 mins at room temperature until dissolved. The solution was centrifuged at 16000 g for 10 mins to remove undissolved solids. Supernatant was removed and acidified by adding 1.335 ml 10N HCL for 30 mins. The acidified solution was neutralised by adding 1.555 ml 10M NaOH and the pH measured, pH-7.0. The final solution was filtered through a 0.45 um filter and then through a 0.2 um filter to sterilise. A 6% solution was used as the stock solution for the trial (i.e. stock solution was diluted 1/8 or 1/12 into formula).

Example 2

In Vitro Immuno-Regulatory Activity of Acid Treated Aqueous Soluble Whey Protein-Containing Component The extract (I23) formed in Example 1 was tested for in vitro immuno-regulatory activity in a number of cell based assays. The extract was aliquoted into 96 well plates and then screened in rapid cell based screening assays.

Figure 1:
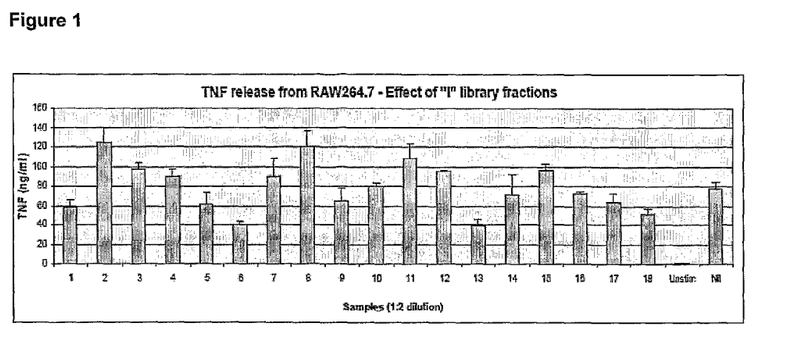
FIG. 1. Inhibition of TNF alpha release from RAW cells after treatment with extract (I23).

Data in FIG. 1, shows TNF alpha (a Th1 cytokine) release in vitro by RAW cells which are a macrophage cell line. I23 stimulated TNF alpha production in RAW cells (see fraction number 3 in FIG. 1).

Figure 2:
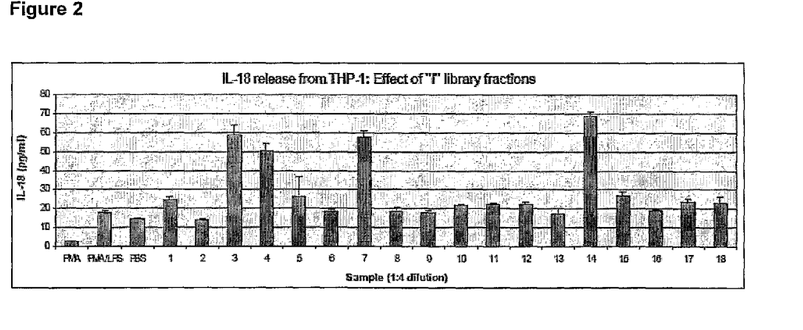
FIG. 2. Enhancement of IL-18 release from THP-1 cells after treatment with extract (I23).

IL-18 is a major early immuno-regulatory cytokine which drives T cell development into either a Th1 (inflammation) or Th2 (allergy) direction depending on the surrounding cytokine milieu. We also assessed IL-18 secretion after phorbol 12-myristate 13-acetate (PMA) with or without lippopolysaccharide (LPS) stimulation of THP1 cells (a monocyte cell line). Control cells were in Phosphate buffered saline (PBS). Fraction I23 stimulated IL-18 production from THP1 cells (see fraction number 3 in FIG. 2).

Figure 3:
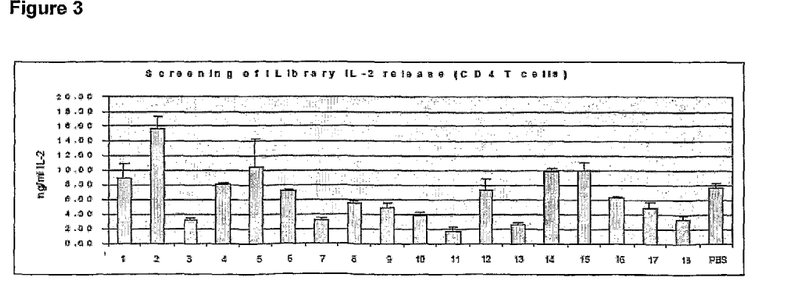
FIG. 3. Inhibition of IL-2 release from Primary CD4 T cells after treatment with extract (I23).

IL-2 is a cytokine which is essential for T cell activation and is critical in immune response induction. We assessed I23 for ability to influence IL-2 release in TGR Biosciences primary T cell assay. T cells were purified from peripheral blood (Buffy coat containing leukocytes were obtained from the Red Cross Blood Bank, Adelaide) using MACS magnetic bead technology (Miltenyi Pty. Ltd). An indirect purification of CD4$^+$ T cells was carried out. Unwanted cells (i.e. CD 8$^+$ lymphocytes, macrophages, B cells etc) were first labelled with magnetic bead conjugated antibodies to the relevant cell surface markers. Labelled cells were then run down a MACS magnetic column, unwanted cells bind to the column leaving CD4$^+$ T cells in the column effluent. These CD4$^+$ T cells were washed and incubated with PMA to stimulate the cells for cytokine production as well as the milk fractions in the library. IL-2 release was assessed by ELISA (see FIG. 3).

Figure 4:
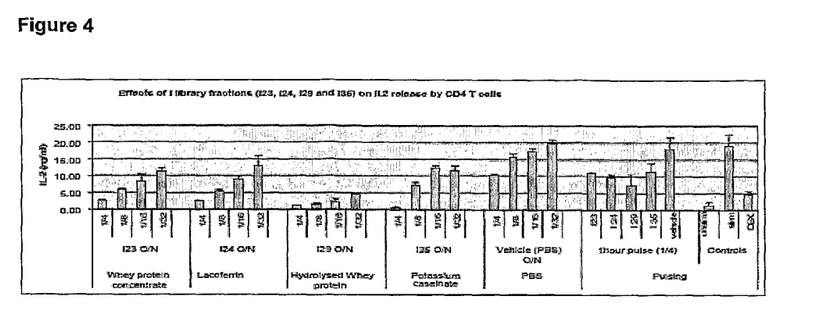
FIG. 4. Effect of extract (I23) on IL-2 release by CD4 T cells

I23 (Fraction 3 in FIG. 3) suppresses IL-2 cytokine release in vitro as demonstrated by mitogenic activation of human CD4$^+$ T cells. IL-2 release was dose dependent after PMA stimulation. Short and long term suppression of the production of IL-2 by I23 was assessed by using an overnight (O/N) incubation or a pulse for 1 hour (see FIG. 4).

We identified 4 potential fractions with in vitro immuno-regulatory activity. The I23 fraction in FIG. 4 induced a dose responsive inhibition of T-cell activation as measured by IL-2 release. Inhibition of IL-2 occurs in T cells incubated with the fractions for 24 hour as well as after a short 1 hour pulse.

Figure 5:
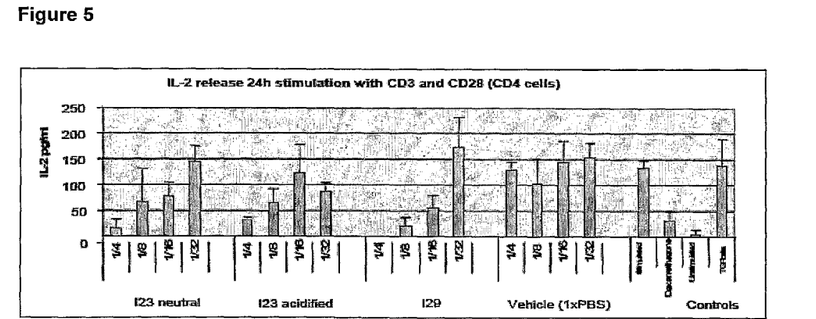
FIG. 5. Effect of extract (I23) (acidified or neutral) on IL-2 release by CD4 T cells after CD3 and CD28 stimulation.

Purified human CD4$^+$ T cells were stimulated overnight with PHA and PMA, in the presence of I23. I23 clearly inhibits IL-2 secretion as evident in a dose ranging study, as a reduction in I23 concentration leads to increased IL-2 secretion. The maximal level of suppression is comparable to that of unstimulated cells and a known immunosuppressant, Dexamethasone. (DEX). For T cells, to be activated in vivo antigen is presented to the T cell receptor and co-stimulatory molecules are activated leading to T cell activation and cytokine release. To further confirm the immuno-regulatory activity we assessed inhibition of IL-2 release after stimulation of the CD4$^+$ T cells via the T cell receptor cell using anti-CD3 antibody, and anti-CD28 (antibody against a co-stimulatory molecule). This activation protocol was set up to mimic what occurs naturally in vivo as a comparison to the non specific mitogenic stimulation of the CD4$^+$ T cells with PHA/PMA. I23 suppresses IL-2 secretion by CD4$^+$ T cells which have been activated with anti-CD3 and anti-CD28 antibodies (see FIG. 5).

Figure 6:
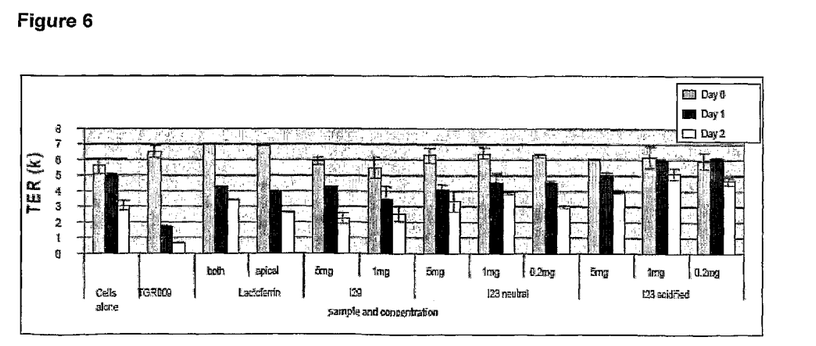
FIG. 6. Tran epithelial resistance of T84 cells after treatment with neutral or acidified extract (I23) or Lactoferrin.
Figure 7:
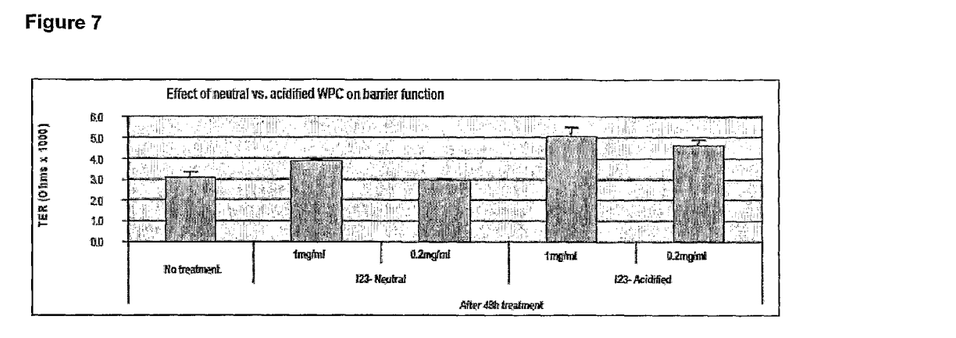
FIG. 7. Trans epithelial resistance of T84 cells after treatment with extract either neutral (I23-neutral) or acid activated (I23-Acidified).

We assessed the effect of milk fractions I23 in vitro using the T84 cell epithelial barrier function assay (TGR Biosciences). I23 showed immuno-inhibitory activity in vitro, we included acid activated and neutral I23 and I29 in the barrier function assay. Transepithelial resistance (TER) was measured in T84 intestinal epithelial cells in culture with and without acid activated and neutral I23 (see FIG. 6). A more detail graph of I23 and its affect on TER is shown in FIG. 7. A decrease in TER represents a decrease in barrier function of the cells The data in FIG. 6 shows that I23 either in a neutral form or in an acidified form had no detrimental effect on the epithelial cell barrier integrity after 1 or 2 days of culture (see FIG. 6 and FIG. 7). However, it did significantly increase the barrier function of the cells in the TER assay.

Resolution of allergy occurs in infants with cow's milk allergy when there is a shift from Th2 to a Th1 type of immune response. I23 also promoted production of the Th1 cytokine IL-18 from THP1 cells (see FIG. 2, fraction 3). Therefore we went onto carry out an in vivo trial with I23 in Brown Norway rat pups.

Example 3

In Vivo Immuno-Requlatory Activity of Acid Treated Aqueous Soluble Whey Protein-Containing Component An in vivo trial using Brown Norway allergy prone rat pups was carried out. Acid activated I23 was given as a continuous infusion mixed into the formula or as a 0.1 ml bolus into the stomach three times a day. The trial was completed with an n=8/group and serum analysis carried out.

I23 has immuno-regulatory activity when used as a supplement into formula (1/8 of a 6% starting solution) or when given as a bolus 3 times/day to formula fed rat pups. A significant decrease in IgE was obtained when compared to IgE levels in rat pups receiving formula alone. One Way ANOVA with a Tukey's post-hoc test was used to assess significance between groups *=P<0.05 treatment group compared to formula fed group.

Figure 8:
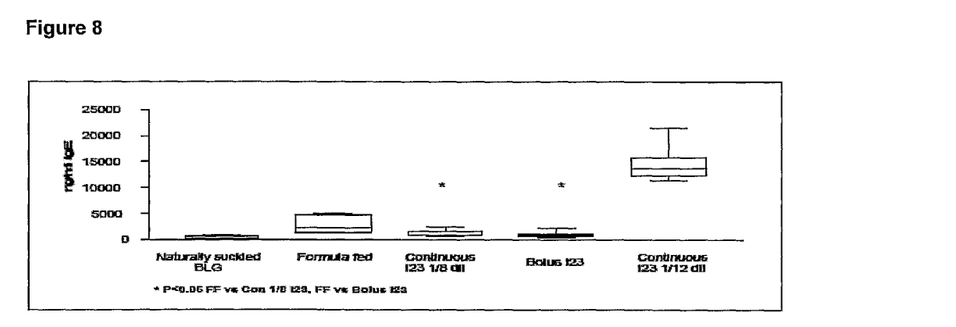
FIG. 8. Serum IgE after extract (I23) treatment at a 1/8 or a 1/12 dilution into formula or as a bolus dose 3 times/day.
Figure 9:
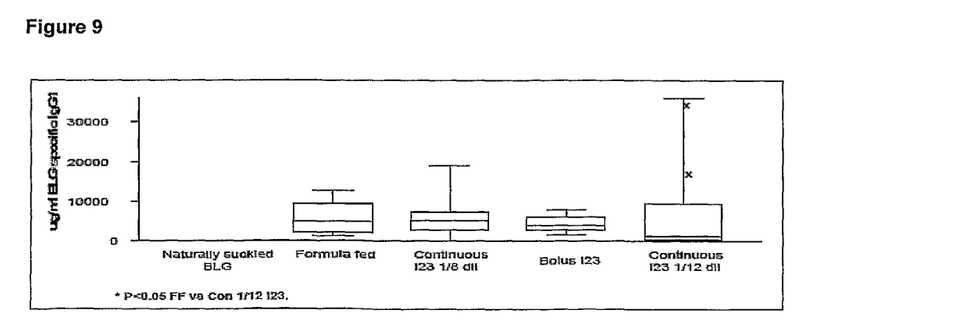
FIG. 9. BLG specific IgG1 concentration after extract (I23) treatment at a 1/8 or a 1/12 dilution into formula or as a bolus dose 3 times/day (outliers included; indicated by x).
Figure 10:
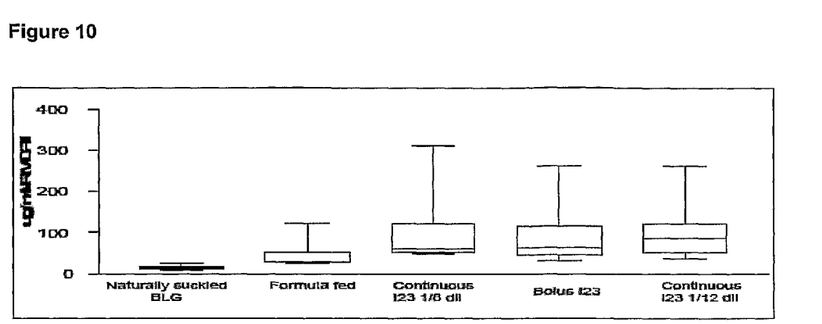
FIG. 10. Serum RMCPII concentration after extract (I23) treatment at a 1/8 or a 1/12 dilution into formula or as a bolus dose 3 times/day.

I23 supplementation of formula at a 1/8 dilution or as a gavage given 3 times a day reduced serum IgE levels compared to formula fed rat pups (see FIG. 8). BLG specific IgG1 was not significantly different from the formula fed group after I23 supplementation at 1/8 or as a bolus dose 3 times a day. However at a 1/12 dilution a decreased IgG1 titre was obtained in 6 out of 8 rat pups, there were two rats in the 1/12 trial with abnormally high serum titres, if the outliers are removed the titre is significantly reduced. Data in FIG. 9 is presented with the outliers serum data included, outliers are identified on the graph with an (x). RMCPII levels were not reduced by I23 treatment (see FIG. 10).

Figure 11:
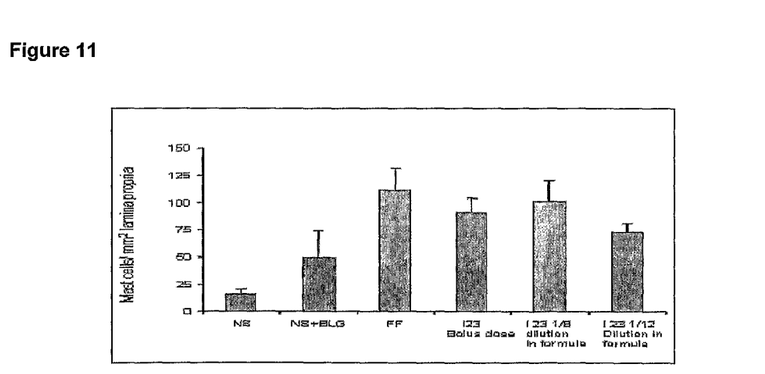
FIG. 11. Mast cell counts/mm2 lamina propria after extract (I23) treatment at a 1/8 or a 1/12 dilution into formula or as a bolus dose 3 times/day.

Mast cell numbers were also counted in the lamina propria after I23 supplementation of formula (see FIG. 11). Mast cell numbers in the lamina propria were reduced in rat pups given I23 after supplementation of the formula at a 1/12 dilution.

Figure 12:
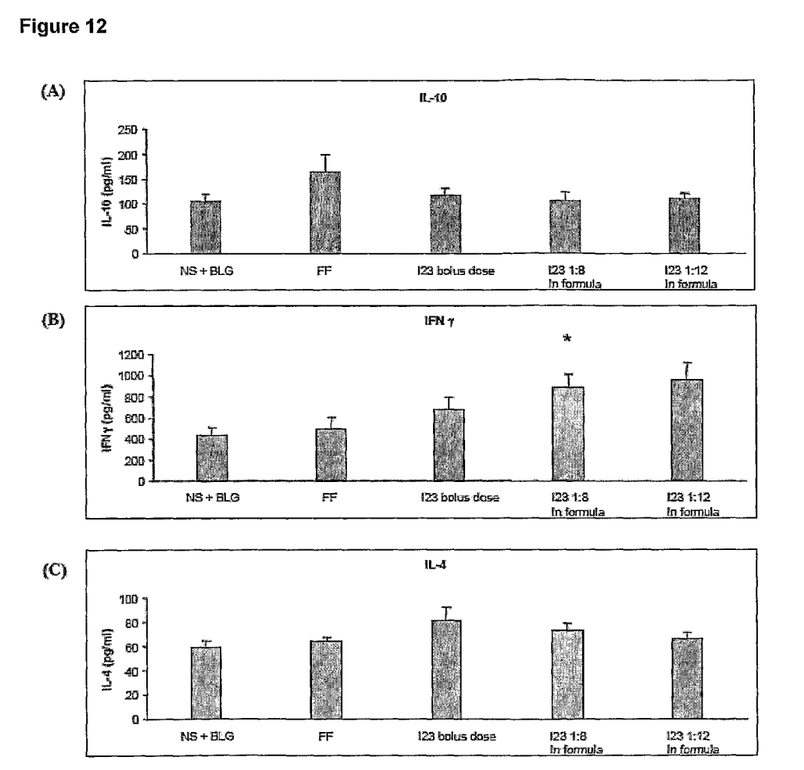
FIG. 12. IL-10 (A), IFN gamma (B) and IL-4 (C) in the intestine after treatment with extract (I23) at a 1/8 or a 1/12 dilution to formula or as a bolus dose 3 times/day.

Cytokines IL-10, interferon gamma and IL-4 were also assayed in intestinal homogenates after I23 supplementation of the diet (see FIGS. 12 (A), (B) and (C) respectively). No significant differences were detected in IL-10 and IL-4 levels between the groups. I23 supplementation of formula at a 1/8 or 1/12 dilution enhanced IFN gamma concentrations in the intestine. Infants who go onto resolve their cow's milk allergies have increased IFN gamma levels compared to infants who go onto have persistent allergy. I23 appears to promote a shift away from a Th2 response and increasing the Th1 response needed for a balance immune system.

We have identified a milk bioactive with immuno-regulatory activity. I23 when used as a supplement into formula (1/8 dilution of a 6% starting solution) or when given as a bolus dose 3 times/day to formula fed rat pups resulted in a significant decrease in IgE (antibody associated with allergy development) compared to the rat pups receiving formula alone.

Figure 13:
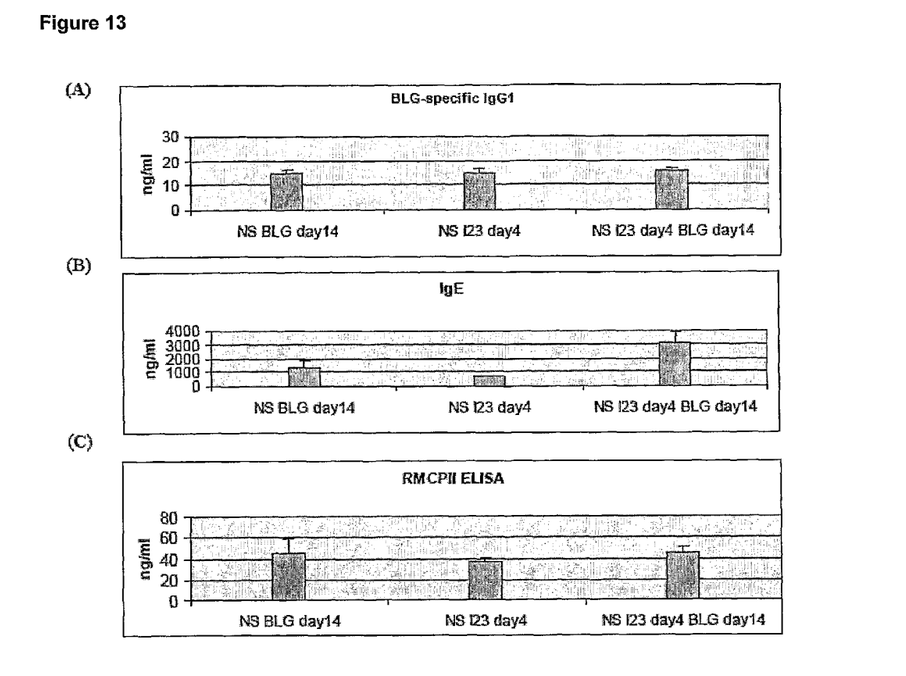
FIG. 13. Weaning study: Serum BLG specific IgG1(A), IgE (B) and RMCPII (C). Gavage with extract (I23) commenced on day 4 and oral BLG commenced at day 14.

We have also carried out a weaning trial and assessed the serum antibody response of rat pups gavaged with I23, acid activated and non acid activated I23. The trial was done to determine if I23 can also regulate the immune response to food antigens at weaning. We commenced gavage with I23 at day 14 in the trial. Our recent data from the ontogeny study suggested that supplementation of the infant diet needs to occur at an earlier age. To determine if pre-treatment with I23 influenced the immune response to food antigens at weaning we carried out a second trial where we commenced feeding I23 at day 4 and started BLG at day 14 (see FIGS. 13 A, B and C). I23 in the absence of a BLG challenge reduced the overall concentration of total IgE in serum. Immuno-modulation by dietary supplements as determined by our ontogeny study appears to be more effective if commenced in early life along with specific antigen challenge i.e. in the suckling period.

The invention claimed is:

1. A process for the production of a whey protein extract from a whey protein-containing composition, said process comprising:
   contacting a whey protein-containing composition with an aqueous solution, thereby forming a sample including a soluble protein-containing component and an insoluble component;
   recovering the soluble protein-containing component from the sample;
   acidifying the soluble protein-containing component; and
   neutralizing the acidified soluble protein-containing component;
   thereby forming the whey protein extract, wherein the whey protein containing composition is whey protein concentrate (WPC), and the WPC is WPC 80.

2. The process of claim 1 wherein the whey protein concentrate (WPC) is provided in the form of a powder for contact with the aqueous solution.

3. The process of claim 1 wherein the aqueous solution is water.

4. The process of claim 1 wherein the whey protein concentrate (WPC) is provided for contact with the aqueous solution in an amount of 0.5% to 10% whey protein-containing composition w/w.

5. The process of claim 1 wherein the soluble protein-containing component is recovered by separating the soluble protein-containing component from the insoluble component.

6. The process of claim 5 wherein the soluble protein-containing component is separated from the insoluble component by subjecting the sample to one or more of centrifugation, chromatography, ion exchange, electrodialysis, filtration or adsorption.

7. The process of claim 1 wherein the soluble protein-containing component is acidified by providing a pH of 2.5 to 6.0 to the soluble protein-containing component.

8. The process of claim 1 wherein the acidified soluble protein-containing component is neutralised by providing a pH of 6.5 to 7 to the soluble protein-containing component.

* * * * *

UNITED STATES PATENT AND TRADEMARK OFFICE
CERTIFICATE OF CORRECTION

PATENT NO.        : 9,066,526 B2
APPLICATION NO.   : 13/501819
DATED             : June 30, 2015
INVENTOR(S)       : Irmeli Penttila et al.

It is certified that error appears in the above-identified patent and that said Letters Patent is hereby corrected as shown below:

Title Page, Item 73

Please add the following 2nd assignee:

Women's and Children's Health Research Institute, North Adelaide (AU)

Signed and Sealed this
Fifth Day of July, 2016

Michelle K. Lee
*Director of the United States Patent and Trademark Office*